United States Patent
Lee et al.

(10) Patent No.: US 9,384,982 B2
(45) Date of Patent: Jul. 5, 2016

(54) DEPOSITING MATERIAL INTO HIGH ASPECT RATIO STRUCTURES

(71) Applicant: FEI Company, Hillsboro, OR (US)

(72) Inventors: Sang Hoon Lee, Forest Grove, OR (US); Jeffrey Blackwood, Portland, OR (US); Stacey Stone, Brno (CZ)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 14/758,043

(22) PCT Filed: Dec. 30, 2013

(86) PCT No.: PCT/US2013/078354
§ 371 (c)(1),
(2) Date: Jun. 26, 2015

(87) PCT Pub. No.: WO2014/106202
PCT Pub. Date: Jul. 3, 2014

(65) Prior Publication Data
US 2015/0340235 A1    Nov. 26, 2015

Related U.S. Application Data

(60) Provisional application No. 61/747,509, filed on Dec. 31, 2012.

(51) Int. Cl.
*H01L 21/76* (2006.01)
*H01L 21/31* (2006.01)
*H01L 21/469* (2006.01)
*H01L 21/26* (2006.01)
(Continued)

(52) U.S. Cl.
CPC .......... *H01L 21/2605* (2013.01); *C23C 16/045* (2013.01); *C23C 16/047* (2013.01); *H01L 21/0262* (2013.01); *H01L 21/02115* (2013.01); *H01L 21/02277* (2013.01); *H01L 21/28556* (2013.01); *H01L 21/76879* (2013.01); *H01L21/76898* (2013.01); *H01L 21/0243* (2013.01); *H01L 21/02636* (2013.01)

(58) Field of Classification Search
CPC ..... H01L 21/205; H01L 21/469; H01L 21/31; H01L 21/76
USPC .................................................. 438/758, 435
See application file for complete search history.

(56) References Cited

U.S. PATENT DOCUMENTS 5,429,730 A    7/1995    Nakamura et al.
5,435,850 A    7/1995    Rasmussen
(Continued)

FOREIGN PATENT DOCUMENTS

KR    1020090019865    2/2009

*Primary Examiner* — Karen Kusumakar
(74) *Attorney, Agent, or Firm* — John B. Kelly; Scheinberg & Associates, P.C.

(57) ABSTRACT

A method is provided, along with a corresponding apparatus, for filling a high aspect ratio hole without voids or for producing high aspect ratio structures without voids. A beam having a diameter smaller than the diameter of the hole is directed into the hole to induced deposition beginning in the center region of the hole bottom. After an elongated structure is formed in the hole by the beam-induced deposition, a beam can then be scanned in a pattern at least as large as the hole diameter to fill the remainder of the hole. The high aspect ratio hole can then be cross-sectioned using an ion beam for observation without creating artefacts. When electron-beam-induced deposition is used, the electrons preferably have a high energy to reach the bottom of the hole, and the beam has a low current, to reduce spurious deposition by beam tails.

19 Claims, 12 Drawing Sheets

(51) Int. Cl.
  *H01L 21/02* (2006.01)
  *H01L 21/285* (2006.01)
  *C23C 16/04* (2006.01)
  *H01L 21/768* (2006.01)

(56) References Cited

U.S. PATENT DOCUMENTS

| | | | |
|---|---|---|---|
| 5,851,413 A | 12/1998 | Casella et al. | |
| 7,888,273 B1 | 2/2011 | Wang et al. | |
| 7,981,763 B1 | 7/2011 | van Schravendijk et al. | |
| 2003/0198755 A1 | 10/2003 | Shichi et al. | |
| 2004/0058507 A1* | 3/2004 | Ho | H01L 21/76224 438/424 |
| 2007/0059900 A1* | 3/2007 | Lai | H01L 21/31116 438/435 |
| 2007/0298585 A1 | 12/2007 | Lubomirsky et al. | |
| 2011/0151678 A1 | 6/2011 | Ashtiani et al. | |
| 2015/0243478 A1 | 8/2015 | Lee et al. | |

\* cited by examiner

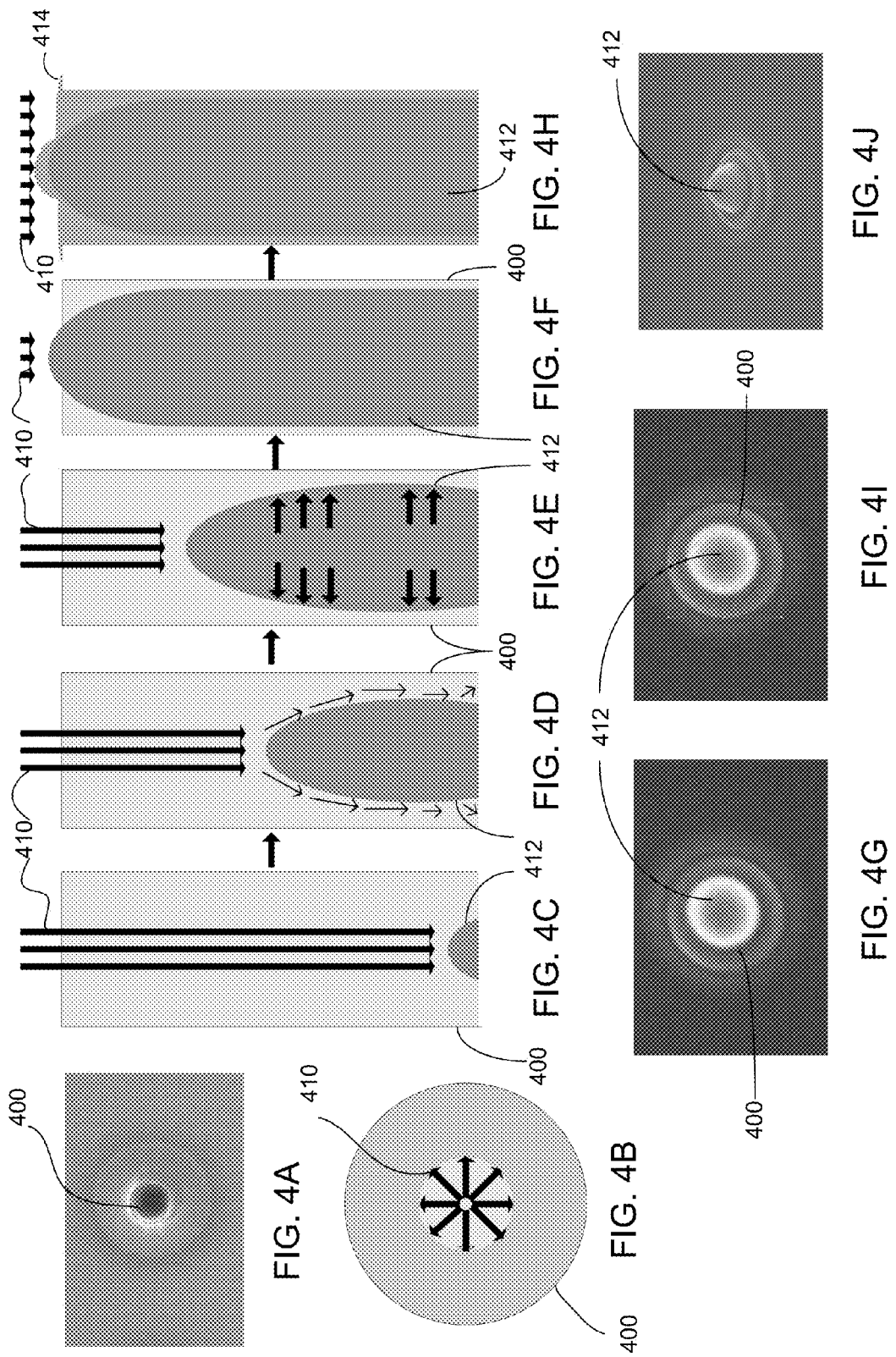

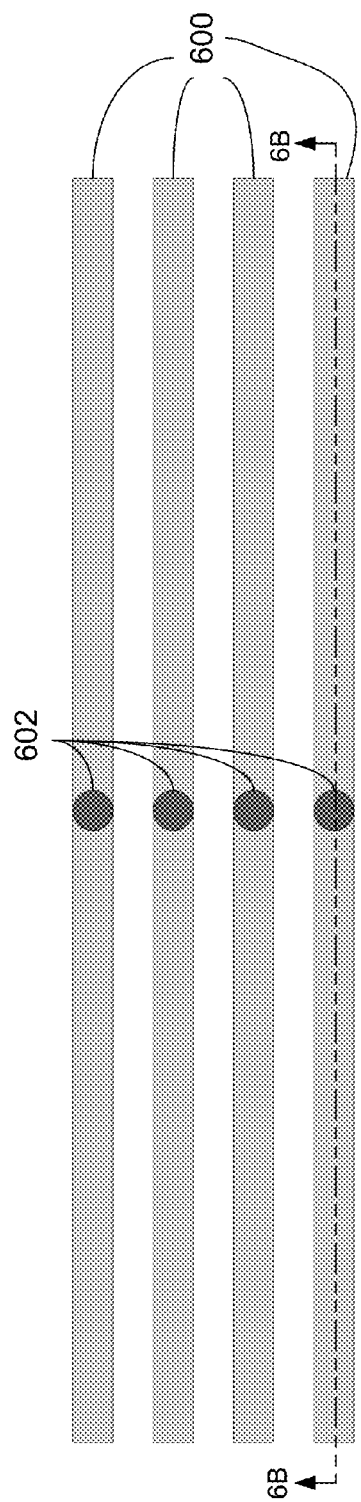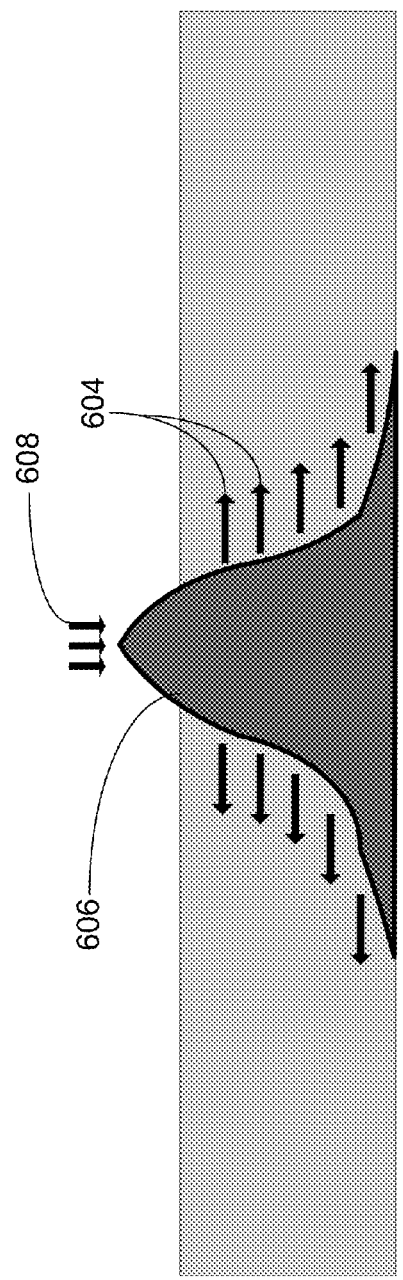

DEPOSITING MATERIAL INTO HIGH ASPECT RATIO STRUCTURES

TECHNICAL FIELD OF THE INVENTION

The present invention relates to forming nanoscale structures in particular to filling high aspect ratio structures using beam-induced deposition.

BACKGROUND OF THE INVENTION

Structures forming integrated circuits and other nanotechnology have dimension on the nanometer scale. Many processes that were useful for structures on a larger scale are not adequate for processing structures on a nanoscale. One method of observing the structures for process development, process control, and defect analysis is to expose a portion of the structure using a focused ion beam and observe the exposed structure using a scanning electron microscope (SEM) or a transmission electron microscope (TEM). When the ion beam mills material to expose a structure for observation, the ion beam can distort the structure and create artifacts that interfere with the observation.

A high aspect ratio (HAR) structure is a structure having a height that is much greater than its width. For example, a feature having a height three times greater than its width would be considered a high aspect ratio feature. For example, a hole between layers in an integrated circuit may have a height that is several times greater than its width. In analyzing high aspect ratio structures, such as unfilled contacts or vias, in integrated circuits, such as 3D NAND circuits used in flash memory, the conventional ion beam sample preparation process causes conspicuous artifacts, such as structure distortion, and the ion beam curtain effect.

The ion beam curtain effect, or curtaining, occurs when materials are removed at different milling rates. This can happen when milling a feature comprised of multiple materials that are removed at different rates by the same beam. This can also happen when milling a surface having an irregular shape. For example, a feature of interest can be a through-silicon vias (TSV). Cross-sectioning TSVs is a common practice in semiconductor labs to characterize voids and surface interfaces. Due to the depth of TSVs (typically 50-300 nm), milling a cross section of a TSV with an ion beam can result in substantial curtaining.

When there are unfilled holes on a sample, there are large differences in the milling rates between the material and areas adjacent to the open area or hole. The large difference in milling rates results in curtaining or waterfall effects that distort the shape of the hole. Structure damage and artifacts of the ion beam process make it difficult to perform high aspect ratio vertical structure analysis.

Because of the damage and artifacts caused by the ion beam milling to expose the features, the images do not faithfully show the results of the fabrication process. This interferes with measurements and with an assessment of the fabrication process since the image and measurements show the results of the sample preparation and not just the manufacturing process.

Typically ion beam-induced deposition is used to fill holes in preparing semiconductor structures for analysis. In filling high aspect ratio holes using charged particle beam-induced deposition, voids are often created as the filling of the hole is uneven, and the filling tends to pinch off a region, closing it off to the beam and the precursor gas.

As the device structure decreases in size, less than 100 nm range critical dimension (CD), and the number of layers increases, new fabrication technologies face huge demands, such as creating finely stacked layers on complex structures like deep trenches, high aspect ratio (HAR) structures, channel holes or channel lines with diameters less than 20 nm, including features on temperature-sensitive and energy-sensitive materials like high-K polymer materials for IC devices. So far, conventional technology is unable to fill gaps locally without creating voids in filling structures or without causing artifacts, such as structure distortion, or the ion beam curtain effect.

A method for filling high aspect ratio holes without altering the structure or creating artifacts is needed.

SUMMARY OF THE INVENTION

An object of the invention is to provide a method and apparatus for filling microscopic high aspect ratio holes without creating voids.

In accordance with some embodiments of the invention, charged particle beam-induced deposition is used to deposit a structure within a hole and away from the walls of the hole, typically in the middle of the hole. In accordance with some embodiments of the invention, a structure is deposited using electron beam induced deposition, with the electron beam having a relatively high energy. The structure is deposited by directing the beam in a pattern that does not overlap the edges of the hole and that covers typically less than fifty percent of the area of the hole cross section and then in a second pattern that overlaps the edges of the hole and completes the filling process.

By eliminating any artifacts, embodiments provide reliable failure analysis (FA) results for the high aspect ratio 3D IC structure process and other high aspect ratio processes including holes, trenches, and other structures.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

FIG. 4A shows an image of a top view of a high aspect ratio hole. FIG. 4B shows a preferred beam scanning pattern in which the beam is scanned in a circular pattern of increasing diameter in the center hole. FIG. 4C shows the hole beginning to be filled using an embodiment of the invention. FIGS. 4D to 4F shows the hole of FIG. 4C being progressively filled using a first scan pattern. FIG. 4G is a photomicrograph corresponding to the drawing of FIG. 4F and showing a hole after a filling using the first scan pattern. FIG. 4H shows a hole being filled using a second scan pattern after the first scan pattern. FIG. 4I shows a top view of a hole after completion of the second scan pattern of FIG. 4H. FIG. 4J is an angled view of the filled hole of FIG. 4I.

FIG. 6A shows a high aspect ratio channel partly filled in accordance with an embodiment of the invention. FIG. 6B shows a cross section of the filling in the channel.

DETAILED DESCRIPTION OF PREFERRED EMBODIMENTS

When forming a cross section of a region of a sample that includes a high aspect ratio hole, artifacts in the cross section arise from voids formed when the holes are filled in a conventional method. By filling high aspect ratios holes without producing voids, no artifacts are created in the cross sectioning and reliable failure analysis results. Filling holes is also useful in some applications for creating useful structure.

There are difficulties in filling high aspect ratio holes or channels using a conventional charged particle beam technique. In beam-induced deposition, charged particles or photons induce decomposition of a precursor gas molecule, such as an organometallic molecule like tungsten hex carbonyl ($WCO_6$) or a platinum (Pt) precursor. The precursor is typically in the form of a gas, which is directed toward the work piece surface through a gas injection nozzle. In some embodiments, the entire work piece is in a cell filled with the precursor gas or a portion of the work piece is partially enclosed to create a gaseous environment at the beam impact point on the surface.

It is thought that the relatively high energy charged particles in the primary beam typically do not react directly with the precursor gas molecules. The interaction of the charged particles in the primary beam with the work piece creates low energy secondary electrons that are more likely to cause decomposition of the precursor molecules. A beam of ions may also create lattice vibrations or phonons that induce the reaction between the precursor molecules and the work piece.

As the charged particle beam causes decomposition of the deposition precursor molecules at the surface to deposit a material, additional gas molecules diffuse to the surface to continue the beam-induced deposition reaction. In the bottom of a high aspect ratio hole, the gas molecules do not replenish as rapidly as on the surface. Also, the number of secondary electrons generated depends on the work piece material and geometry. More secondary electrons may be generated, for example, at edges, than at flat surfaces. Such inconsistency in gas availability and secondary electron generation causes irregular deposition in high aspect ratio holes, which makes it difficult to fill a high aspect ratio hole without voids.

Figure 1:
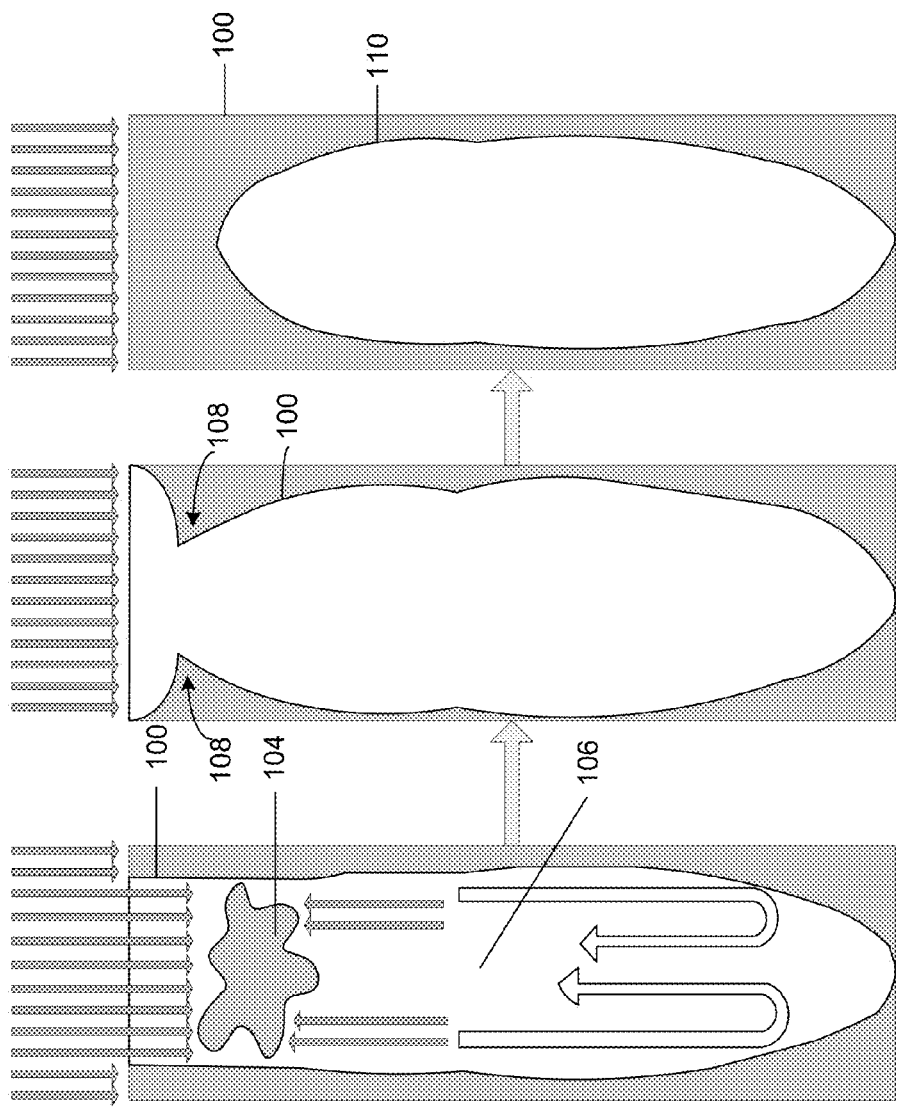
FIG. 1A shows a conventional beam-scanning pattern used to fill a high aspect ratio hole.
FIGS. 1B to 1D shows the progression of the prior art hole-filling process.

FIG. 1A shows a top down view of a conventional rectangular raster beam scan pattern 102, overlaid onto a high aspect ratio hole 100. FIGS. 1B-1D shows the hole 100 being filled by charged particle beam-induced deposition using a local platinum (Pt) gas 104, which creates a bottleneck effect 108 at the upper region of the hole 100 as shown in FIG. 1C, subsequently closing off the hole 100 and leaving a void 110 in the high aspect ratio structure 100 as shown in FIG. 1D. FIG. 1B shows the air flow within the hole, which causes turbulence and updraft 106 of the Pt gas to occur resulting in the bottleneck effect.

Figure 2:
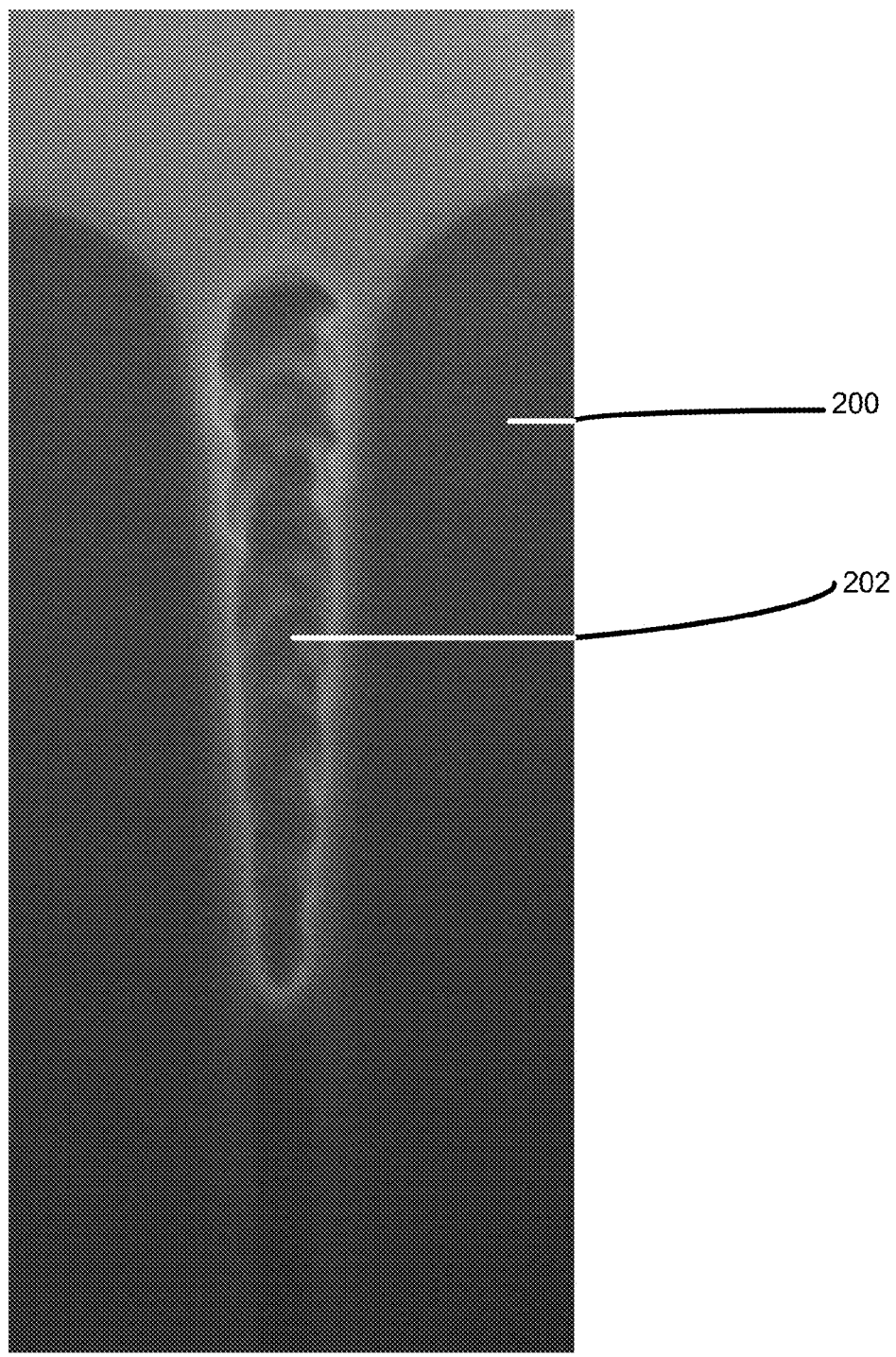
FIG. 2 is a cross-sectional image of a hole filled using a prior art technique, the filling including a void.
Figure 3:
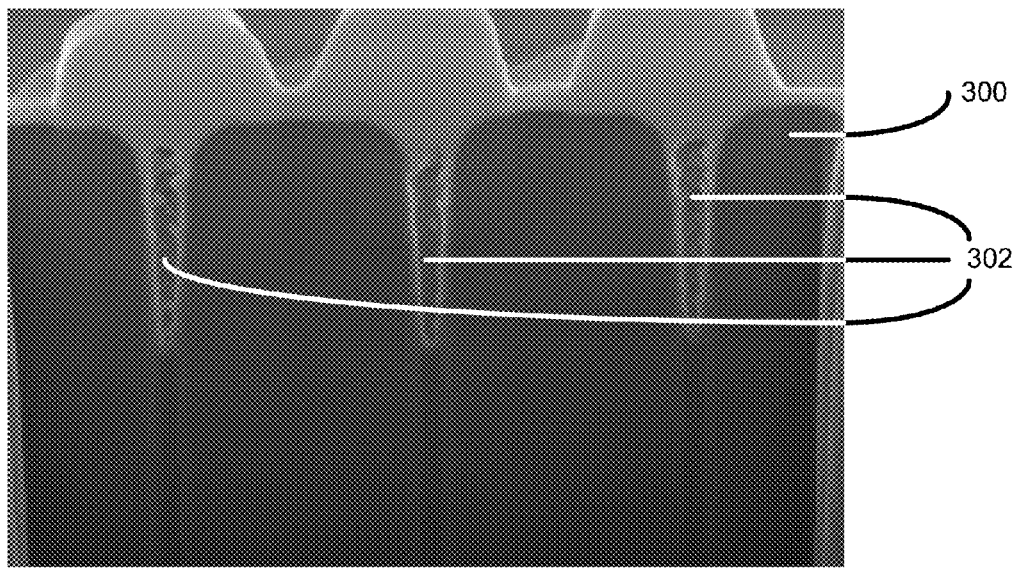
FIG. 3 is a cross-sectional image of several holes filled using a prior art technique, the fillings including voids.

FIGS. 2 and 3 shows cross-sectional views of a voids created using a prior art hole-filling process. FIG. 2 shows single void 202 created in a high aspect ratio structure 200. FIG. 3 shows a cross-sectional view of multiple voids 302 created in a high aspect ratio structure 300.

While ion beam-induced deposition, laser beam-induced deposition, or deposition induced by another energy source can be used with some embodiments, some embodiments use highly accelerated electrons to react with a precursor gas. The use of electrons, instead of ions, gives finer packed layer structures compared to those produced with the accelerated ion deposition process. The precursor gas can decompose to deposit heavy materials like platinum and tungsten or light materials like carbon. The invention is not limited to any specific precursor gases.

In some embodiments, the landing area of the electron beam or other beam has a diameter of $\frac{1}{5}$ to $\frac{1}{10}$ of the diameter of the hole or the width of the channel. In some embodiments, the electron beam is scanned in a first pattern in circles having increasing diameters from the inside of the landing area to the outside of the landing area, toward the wall of the hole. This avoids the creation of voids and creates a 'gas vent direction' with deep penetration to the HAR structure of the precursor gas. Embodiments typically use a higher electron beam landing energy than typically used for electron beam-induced deposition. It is known that lower energy electron beams produces higher resolution deposition patterns because the interaction volume in the work piece is smaller, so secondary electrons, which induce decomposition, come from a smaller region around the beam impact point.

Embodiments of the present invention use relatively high electron beam energies. This energy depends on the material being deposited. In general, skilled persons have considered lower energy electrons better for beam-induced deposition because the interaction volume is smaller. Contrary to the prevailing reasoning, embodiments of the invention typically use higher electron energies. Some applications use an electron beam energy greater than 10 keV, greater than 15 keV, or greater than 20 keV. The higher beam energy increases the mean free path of the electrons in the beam, so that they penetrate further into the hole. Some application use a relatively small beam current, such as less than 500 pA, less than 200 pA, and preferably between 100 pA and 200 pA, which reduces the beam tails to reduce deposition away from the beam axis. For example, one embodiment for filling a high aspect ratio hole with platinum uses a 30 keV electron beam. Another embodiment for filling a hole in a polymer, such as a high-K material, with carbon uses a 5 keV electron beam. Using too high a beam energy can damage the structure of temperature-sensitive and energy-sensitive materials. Depending on the materials, the acceleration voltage range can vary from a few electron volts (eV) to mega electron volts (MeV).

By adjusting the factors of pattern shape, pattern size, and beam energy, all types of structures can be filled and covered by a finer layer of any material without the creation of voids.

Figure 5A:
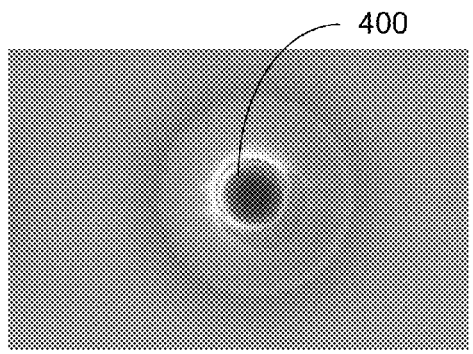
FIG. 5A shows an image of a top view of a high aspect ratio hole of FIG. 4A.

FIGS. 4A-4J show a two-step process of depositing material to fill a hole. The term "hole" is hereby defined as any cavity or depression, regardless of cross section, such as a cylindrical hole, a trench, a square hole, a rectangular hole, an irregular hole, or a jagged hole. FIGS. 5A-5E show results at various stages of the process. One embodiment of the invention scans the hole 400 in circular patterns, the radius increasing to so the deposition progresses from the center outward, at a beam energy specific to the material of the structure, using an electron beam at a beam energy of about 30 keV and a beam current of between about 100 pA to about 200 pA. That is, the beam scans in repeated circular or spiral patterns of increasing diameter up to preferably about ⅕ to 1/10 of the trench width or diameter of the hole. FIGS. 4A and 5A show top views of a high aspect ratio hole 400. FIG. 4B shows how the beam 410 is scanned in circles, with the arrows pointing radially outward from a small circle to indicate circles of increasing diameters. Because the interaction volume is large compared to the beam spot size, the beam could scan in a circle of a single diameter. Depending on the beam spot size, the beam could also be stationary.

Figure 5B:
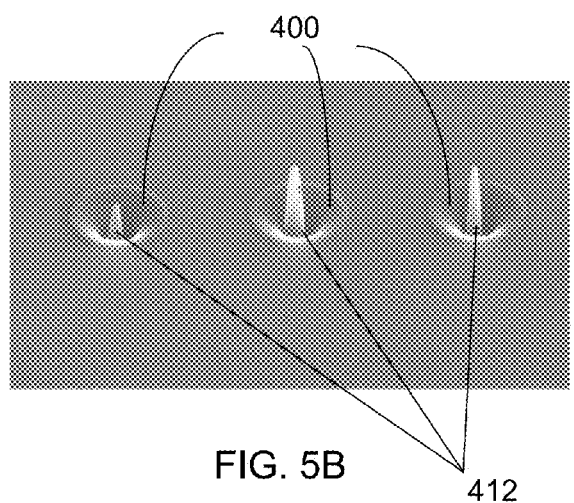
FIGS. 5B-5D are photomicrographs showing a filling process in various stages.

FIG. 4C shows the beam 410 in the first step directed to an area having a cross section about ⅕ to ⅙ the cross section of the hole and shows the beginning of the growth of the deposit 412. FIGS. 4D to 4F shows the growth of the structure 412 in and from the center of the hole 400. The arrows around the outside of the deposited structure in FIG. 4D indicate the flow of deposition gas. The arrows in FIG. 4E show the direction of growth of the walls of the deposited structure. FIG. 4G is an image of the hole after the first processing step. FIG. 5B shows views from 52 degrees of the formation of structures 412 at various stages of processing in the first step. Note that the deposited structures may extend above the plane of the work piece surface in the first step. In one embodiment the processing time for the first step is typically about 5 or 6 seconds per hole.

Figure 5C:
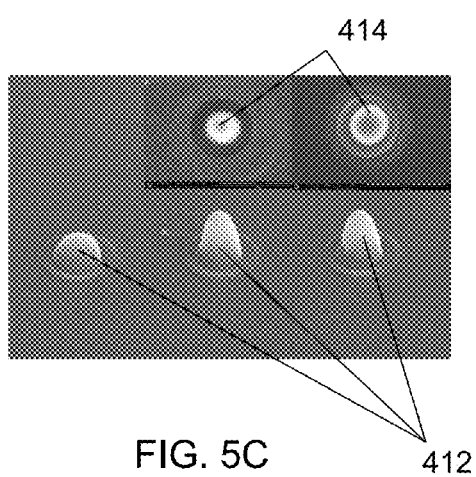
Figure 5D:
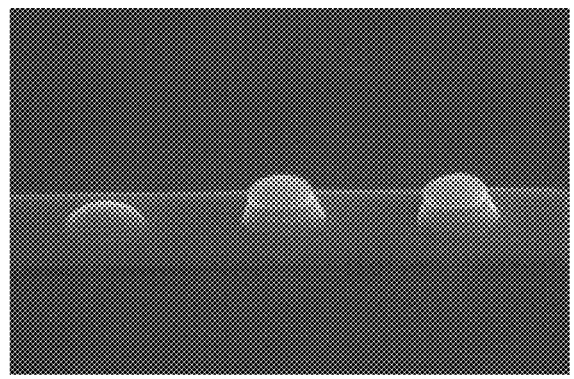
Figure 5E:
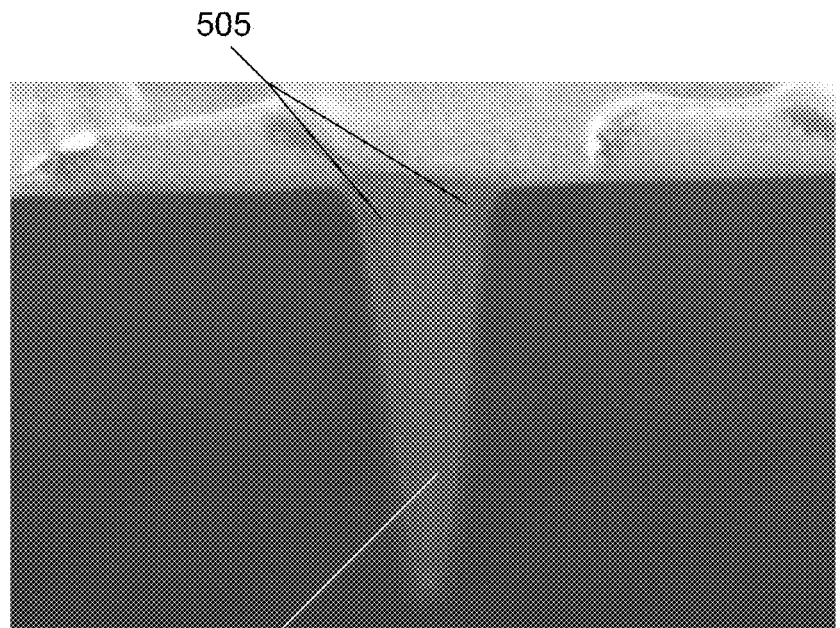
FIG. 5E shows a cross section of a hole filled in accordance with an embodiment of the invention.
Figure 5F:
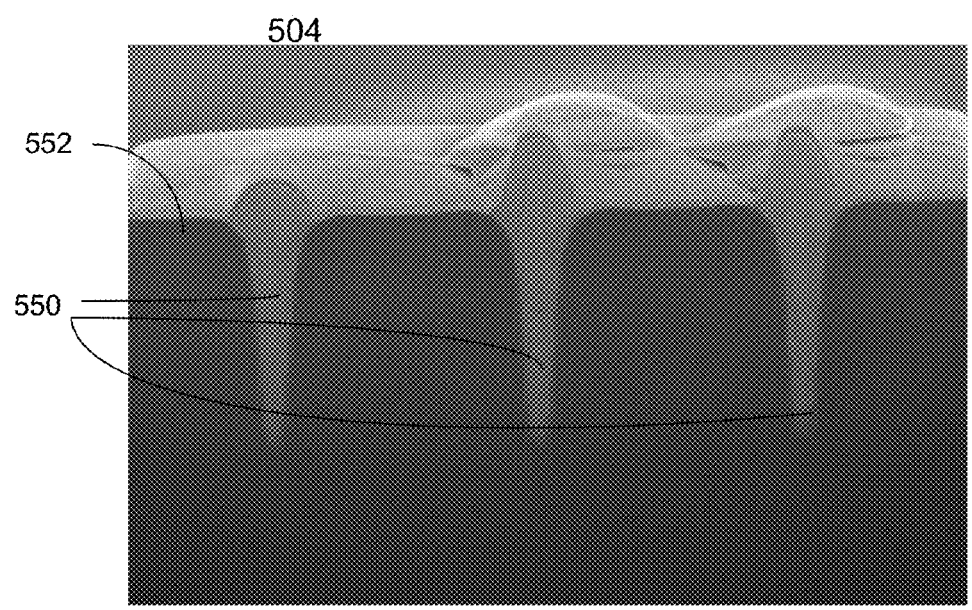
FIG. 5F shows a cross section of multiple high aspect ratio holes filled in accordance with an embodiment of the invention.

In the second step, the diameter of the scan pattern size is set to be approximately twice the trench width or diameter of the hole. FIG. 4H shows the second step of the process, which fills the remainder of the hole and provides a thin layer 414 on the work piece surface around the top of the hole. FIG. 4I shows a top view of the hole 400 after completion of the second step. FIG. 4J shows the completed filled hole 412 at 52 degrees tilt. FIG. 5C shows various stages of structure formation during the second processing step, some showing both a top view 414 and a 52 degree view 412. In one embodiment the second step also takes about 5-6 seconds. In both steps, the time required depends on the beam current, the precursor gas and the size of the hole. FIG. 5D shows the resulting structures of the two step process depicted in FIGS. 5A-5C. FIG. 5E shows a cross-sectional view of the structures after completion of the two-step process. The additions to the structure from the first process 504 and the additions to the structure from the second process 505 can be seen in the cross section of FIG. 5E. FIG. 5F shows a cross sectional view of multiple filled holes 550 in a high aspect ratio structure 552 filled in accordance with the invention.

Figure 5G:
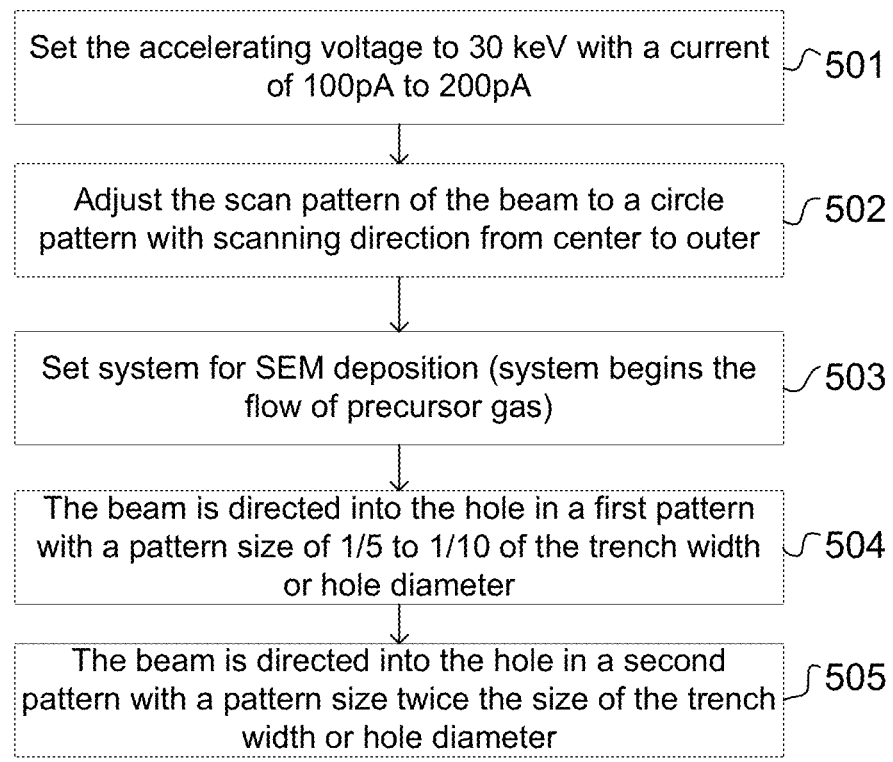
FIG. 5G is a flow chart showing the steps of an embodiment of the invention.

FIG. 5G shows the steps of an embodiment of the invention. Step 501 adjusts the acceleration voltage of the electron beam. The beam energy will depend on the precursor gas being used and on the surface material. For example, for a metallic precursor, the accelerating voltage is set to 30 keV, with a current of 100 pA to 200 pA. A carbon precursor would use a lower beam voltage. The optimum beam voltage can be readily determined by a skilled person for any specific application. Step 502 adjusts the scan pattern of the beam to a series of circle patterns of increasing diameters. Step 503 configures the system for SEM deposition, that is, the system begins the flow of a precursor gas. Step 504 directs the electron beam into the hole in a first pattern, the beam covering an area between ⅕ to 1/10 of the trench width or of the hole diameter. After a spear-shaped structure is deposited into the center of the hole, Step 505 sets the second pattern size as twice the trench width or diameter for the second process and directs the electron beam into the hole in a second pattern, the beam covering an area larger than the hole.

Figure 5H:
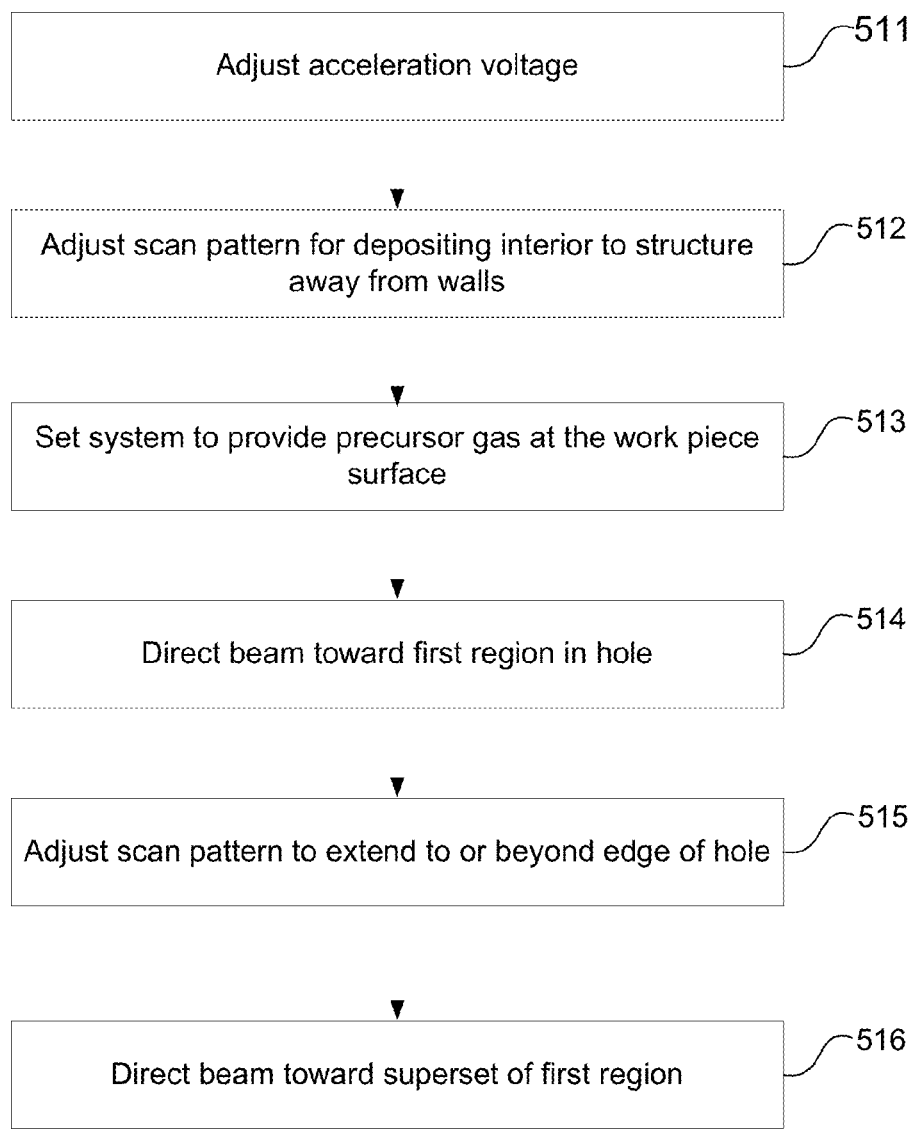
FIG. 5H is a flow chart showing the steps of another embodiment of the invention.

FIG. 5H shows steps of another embodiment of the invention. In Step 511, the beam parameters are adjusted depending upon the precursor gas and the substrate. In Step 512, the beam position or scan pattern is adjusted for depositing material in the interior of the hole to form the structure away from the walls. In Step 513, the system is configured to provide a precursor gas at the work piece surface, such as by a localized gas injection system or by providing an environmental cell containing the gas. In Step 514, the beam is directed towards the first region in the hole. In Step 515, the scan pattern is adjusted to extend to or beyond the edge of the hole. In Step 516, the beam is directed toward the superset of the first region. The beam can be a charged particle beam, such as an electron beam or an ion beam, a laser beam, neutral beam, or any beam that can provide the energy to decompose a precursor gas.

FIG. 6A shows filling of portions 602 of a 20 nm to 30 nm wide channels 600. FIG. 6B shows the cross-sectional view of a high aspect ratio void free structure 606 after filling a hole in the channel. Beginning deposition by the electron beam 608 in the center of the channel causes excess gas to vent outward causing deposition growth in the same direction (arrows 604). This causes the interior of the structure 606 to be void free after the deposition process.

By filling holes or channels without voids, embodiments of the invention reduce the damage and artifacts in holes, channels, or other features when they exposed by ion beam milling. Embodiments are particularly useful for analysis of new three-dimensional structures, such as 3D NAND structures that include unfilled high as aspect ratio holes.

Figure 7:
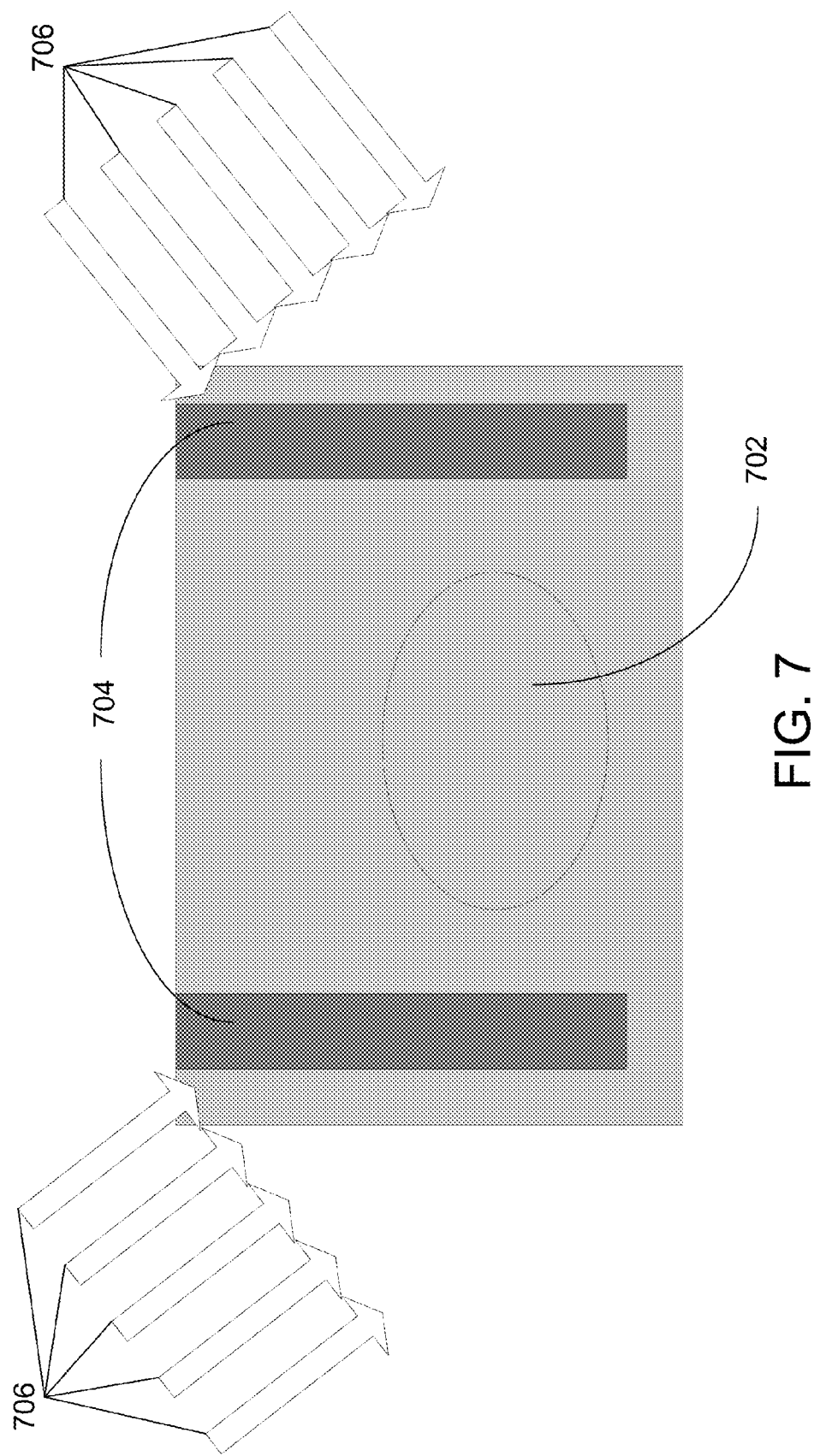
FIG. 7 shows an embodiment of the invention used to mill a region of interest without creating curtaining artifacts.

Ion beam milling artifacts are reduced when a feature of interest immediately follows a uniform region the beam path. The uniform region can be provided by milling and then filling holes so that the beam mills and passes through the filling, just before the beam reaches the feature of interest. FIG. 7 shows an application of the present invention. Holes 704 are milled and then filled. The metal in the deposited material in holes 704 than provides a uniform surface to a focused ion beam before the beam 706 mills the region of interest 702, thereby reducing curtaining.

Figure 8:
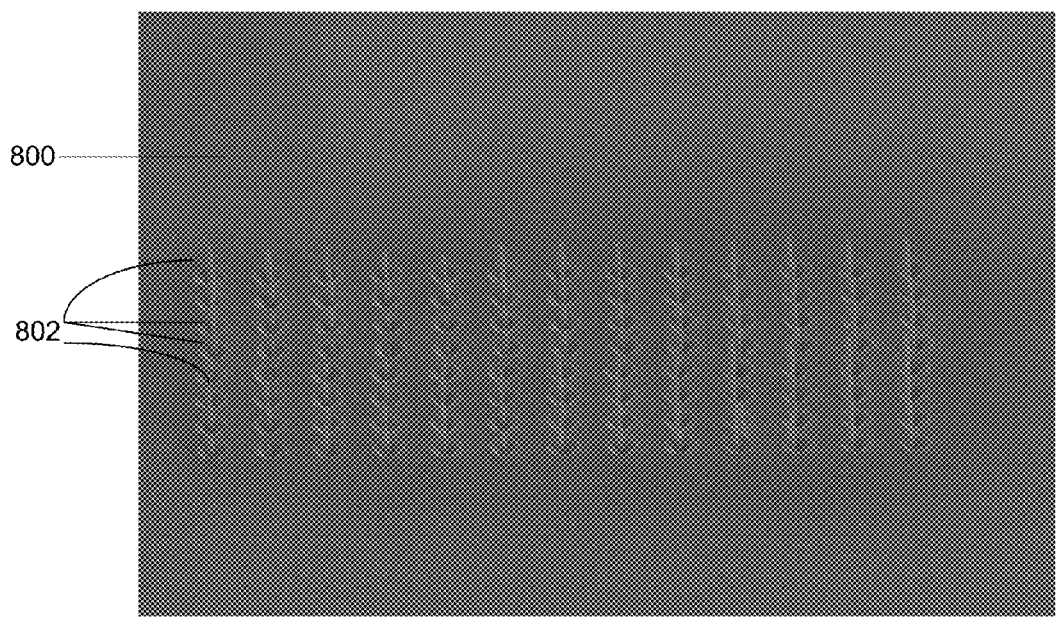
FIG. 8 shows multiple high aspect ratio structures in accordance with an embodiment of the invention.

FIG. 8A shows an angled view of multiple structures formed by filled holes 802 in high aspect ratio structures 800. The invention can be used not only to fill holes to prevent artifacts in ion beam milling but also to create structures that have their own uses.

Figure 9:
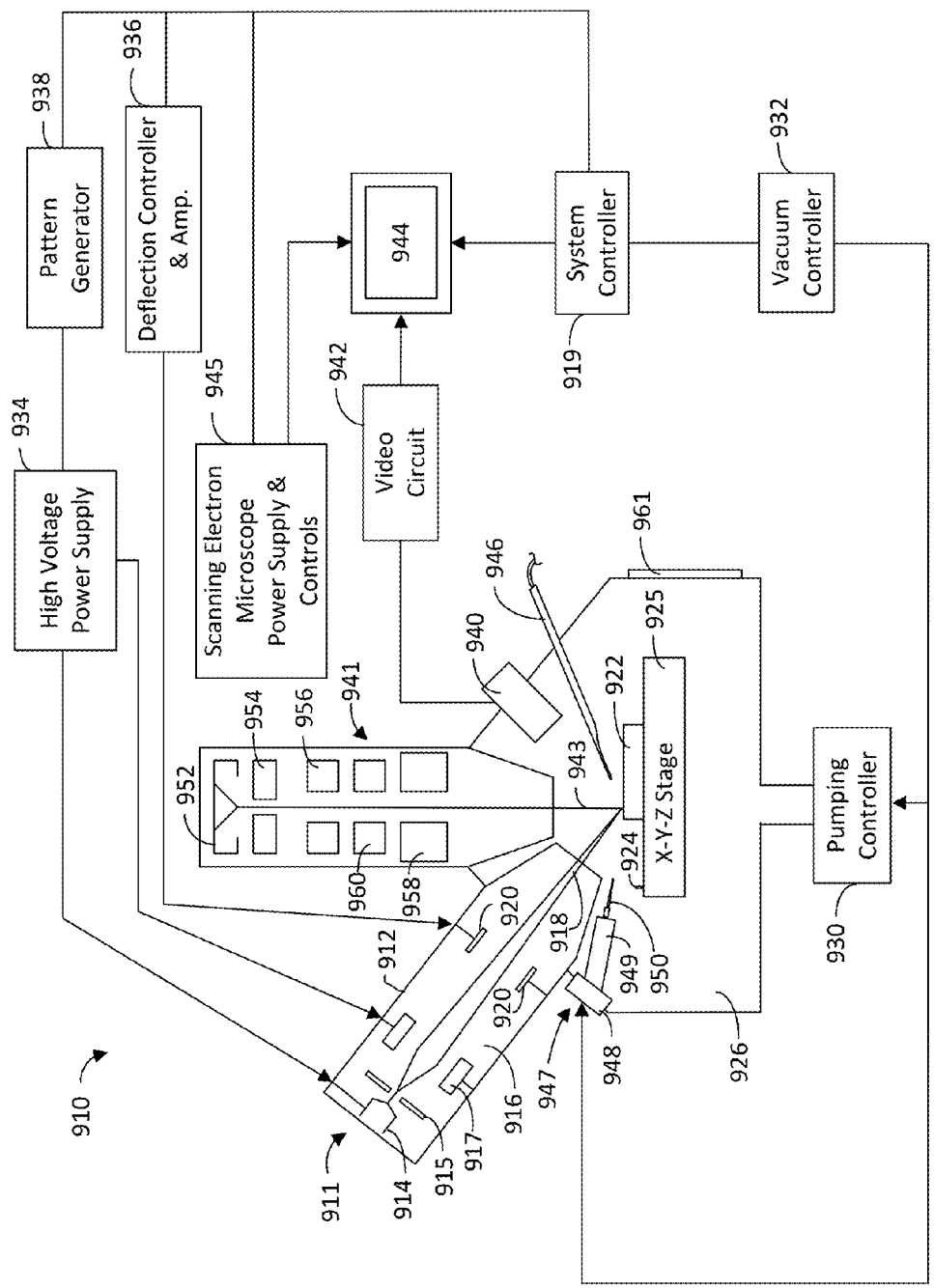
FIG. 9 shows a dual beam system that can be used to implement embodiments of the invention.

FIG. 9 shows a typical dual beam system 910 suitable for practicing the present invention, with a vertically mounted SEM column and a focused ion beam (FIB) column mounted at an angle of approximately 52 degrees from the vertical. Suitable dual beam systems are commercially available, for example, from FEI Company, Hillsboro, Oreg., the assignee of the present application. While an example of suitable hardware is provided below, the invention is not limited to being implemented in any particular type of hardware.

A scanning electron microscope 941, along with power supply and control unit 945, is provided with the dual beam system 910. An electron beam 943 is emitted from a cathode 952 by applying voltage between cathode 952 and an anode 954. Electron beam 943 is focused to a fine spot by means of a condensing lens 956 and an objective lens 958. Electron beam 943 is scanned two-dimensionally on the specimen by means of a deflection coil 960. Operation of condensing lens 956, objective lens 958, and deflection coil 960 is controlled by power supply and control unit 945.

Electron beam 943 can be focused onto substrate 922, which is on movable X-Y-Z stage 925 within lower chamber 926. When the electrons in the electron beam strike substrate 922, secondary electrons are emitted. These secondary electrons are detected by secondary electron detector 940 as discussed below.

Dual beam system 910 also includes focused ion beam (FIB) system 911 which comprises an evacuated chamber having an upper neck portion 912 within which are located an ion source 914 and a focusing column 916. The axis of focusing column 916 is tilted 52 degrees from the axis of the electron column. The ion column 912 includes an ion source 914, an extraction electrode 915, a focusing element 917, deflection elements 920, and a focused ion beam 918. Ion beam 918 passes from ion source 914 through column 916 and between electrostatic deflection means schematically indicated at 920 toward substrate 922, which comprises, for example, a semiconductor device positioned on movable X-Y stage 925 within lower chamber 926.

Stage 925 can preferably move in a horizontal plane (X and Y axes) and vertically (Z axis). Stage 925 can also tilt approximately sixty (60) degrees and rotate about the Z axis. A door 961 is opened for inserting substrate 922 onto X-Y stage 925 and also for servicing an internal gas supply reservoir. The door is interlocked so that it cannot be opened if the system is under vacuum.

An ion pump (not shown) is employed for evacuating neck portion 912. The chamber 926 is evacuated with turbomolecular and mechanical pumping system 930 under the control of vacuum controller 932. The vacuum system provides within chamber 926 a vacuum of between approximately $1 \times 10^{-7}$ Torr and $5 \times 10^{-4}$ Torr. If an etch assisting, an etch retarding gas, or a deposition precursor gas is used, the chamber background pressure may rise, typically to about $1 \times 10^{-5}$ Torr.

The high voltage power supply provides an appropriate acceleration voltage to electrodes in ion beam focusing column 916 for energizing and focusing ion beam 918. When it strikes substrate 922, material is sputtered, that is physically ejected, from the sample. Ion beam 918 or electron beam 943 can decompose a precursor gas to deposit a material.

High voltage power supply 934 is connected to liquid metal ion source 914 as well as to appropriate electrodes in ion beam focusing column 916 for forming an approximately 1 keV to 60 keV ion beam 918 and directing the same toward a sample. Deflection controller and amplifier 936, operated in accordance with a prescribed pattern provided by pattern generator 938, is coupled to deflection plates 920 whereby ion beam 918 may be controlled manually or automatically to trace out a corresponding pattern on the upper surface of substrate 922. In some systems the deflection plates are placed before the final lens, as is well known in the art. Beam blanking electrodes (not shown) within ion beam focusing column 916 cause ion beam 918 to impact onto blanking aperture (not shown) instead of substrate 922 when a blanking controller (not shown) applies a blanking voltage to the blanking electrode.

The liquid metal ion source 914 typically provides a metal ion beam of gallium. The source typically is capable of being focused into a sub one-tenth micrometer wide beam at substrate 922 for either modifying the substrate 922 by ion milling, enhanced etch, material deposition, or for the purpose of imaging the substrate 922. Alternatively, a plasma ion source could be used.

A charged particle detector 940, such as an Everhart Thornley or multi-channel plate, used for detecting secondary ion or electron emission is connected to a video circuit 942 that supplies drive signals to video monitor 944 and receiving deflection signals from controller 919. The location of charged particle detector 940 within lower chamber 926 can vary in different embodiments. For example, a charged particle detector 940 can be coaxial with the ion beam and include a hole for allowing the ion beam to pass. In other embodiments, secondary particles can be collected through a final lens and then diverted off axis for collection.

A micromanipulator 947, such as the AutoProbe 200™ from Omniprobe, Inc., Dallas, Tex., or the Model MM3A from Kleindiek Nanotechnik, Reutlingen, Germany, can precisely move objects within the vacuum chamber. Micromanipulator 947 may comprise precision electric motors 948 positioned outside the vacuum chamber to provide X, Y, Z, and theta control of a portion 949 positioned within the vacuum chamber. The micromanipulator 947 can be fitted with different end effectors for manipulating small objects. In the embodiments described herein, the end effector is a thin probe 950.

A gas delivery system 946 extends into lower chamber 926 for introducing and directing a gaseous vapor toward substrate 922. U.S. Pat. No. 5,851,413 to Casella et al. for "Gas Delivery Systems for Particle Beam Processing," assigned to the assignee of the present invention, describes a suitable gas delivery system 946. Another gas delivery system is described in U.S. Pat. No. 5,435,850 to Rasmussen for a "Gas Injection System," also assigned to the assignee of the present invention. For example, iodine can be delivered to enhance etching, or a metal organic compound can be delivered to deposit a metal.

A system controller 919 controls the operations of the various parts of dual beam system 910. Through system controller 919, a user can cause ion beam 918 or electron beam 943 to be scanned in a desired manner through commands entered into a conventional user interface (not shown). Alternatively, system controller 919 may control dual beam system 910 in accordance with programmed instructions. In some embodiments, dual beam system 910 incorporates image recognition software, such as software commercially available from Cognex Corporation, Natick, Mass., to automatically identify regions of interest, and then the system can manually or automatically extract samples in accordance with the invention. For example, the system could automatically locate similar features on semiconductor wafers including multiple devices, and take samples of those features on different (or the same) devices.

The invention has broad applicability and can provide many benefits as described and shown in the examples above. The embodiments will vary greatly depending upon the specific application, and not every embodiment will provide all of the benefits and meet all of the objectives that are achievable by the invention. Particle beam systems suitable for carrying out the present invention are commercially available, for example, from FEI Company, the assignee of the present application.

Although much of the previous description is directed at semiconductor wafers, the invention could be applied to any suitable substrate or surface. Further, whenever the terms "automatic," "automated," or similar terms are used herein, those terms will be understood to include manual initiation of the automatic or automated process or step. In the following discussion and in the claims, the terms "including" and "comprising" are used in an open-ended fashion, and thus should be interpreted to mean "including, but not limited to . . . ." The term "integrated circuit" refers to a set of electronic components and their interconnections (internal electrical circuit elements, collectively) that are patterned on the surface of a microchip. The term "semiconductor chip" refers generically to an integrated circuit (IC), which may be integral to a semiconductor wafer, singulated from a wafer, or packaged for use on a circuit board. The term "FIB" or "focused ion beam" is used herein to refer to any collimated ion beam, including a beam focused by ion optics and shaped ion beams.

The embodiment above describes a 3D NAND-type structures, but the invention is not limited to such structures and is useful, for example, for DRAMS, and for characterizing trenches and other structures, as well as circular holes. While the embodiments described scan an electron beam in a pattern, the bean could also be a broad beam that covers the desired area without being scanned. It will be understood that at the beam energies used, the interaction area in which secondary electrons are generated to decompose the precursor gas is typically much wider than the beam spot size.

To the extent that any term is not specially defined in this specification, the intent is that the term is to be given its plain and ordinary meaning. The accompanying drawings are intended to aid in understanding the present invention and, unless otherwise indicated, are not drawn to scale.

Some embodiments provide a method of filling a hole using charged particle beam-induced deposition, comprising providing a deposition precursor gas at the surface of the work piece; directing a charged particle beam into a hole having an aspect ratio greater than 3:1, the charged particle beam being directed to a region within the hole having an area less than the cross sectional area of the hole to decompose the precursor gas and deposit material in the hole, the charged particle beam being directed into the hole for a sufficient period of time to form an elongate structure that does not touch the side walls at the top of the hole.

In some embodiments, the method further comprises directing the charged particle beam to cover an area extended beyond the edges of the hole to fill the region between the elongate structure and the hole side walls, thereby filling the hole without voids in the fill material.

In some embodiments, directing the charge particle beam into the hole for a sufficient period of time to form an elongate structure comprises forming an elongate structure that does not contact the top walls of the hole, and further comprising directing the charged particle to an area that is a superset of the first area to finish filling the hole.

In some embodiments, the hole comprises a cylindrical hole and directing the charged particle beam into the hole comprises directing an electron beam in a circular pattern, the diameter of the circular pattern being less than ½ the diameter of the hole.

In some embodiments, the hole is a channel and directing the charged particle beam into the hole comprises directing an electron beam into the channel in a circular pattern having a diameter of less than ½ the channel width.

Some embodiments of the invention provide a method of filling a high aspect ratio hole, comprising providing a deposition precursor gas at the surface of a work piece, the work piece having at least one high aspect ratio hole; directing an electron beam into the high aspect ratio hole, the electron beam being directed in first pattern to impact a region in the hole having a cross section area less than the entire cross sectional area of the hole to deposit an elongate structure into the hole; directing an electron beam toward the work piece in a second pattern to fill the regions of the hole between the elongate structure and the hole side wall, to fill the hole without leaving voids in the fill material.

In some embodiments, directing an electron beam toward the work piece in a second pattern includes directing the electron beam in a second pattern covering an area that includes the entire hole.

In accordance with some embodiments of the invention, providing a deposition precursor gas at the surface of a substrate includes providing a precursor gas that decomposes in the presence of the electron beam to deposit a metal; and directing an electron beam in the first pattern includes directing an electron beam having a landing energy of greater than 5000 eV.

In accordance with some embodiments of the invention, providing a deposition precursor gas at the surface of a substrate includes providing a precursor gas that decomposes in the presence of the electron beam to deposit carbon; and directing an electron beam in the first pattern includes directing an electron beam having a landing energy of greater than 3000 eV.

In some embodiments, directing an electron beam in the first pattern includes directing the electron beam in a circular pattern, the diameter of the circle pattern being less than ¼ the diameter of the hole.

In some embodiments, the method in which the hole is a channel and the diameter of the circle pattern is less than ¼ the channel width.

Some embodiments of the invention provide, a method of filling a high aspect ratio hole, comprising providing a deposition precursor gas at the surface of a work piece, the work piece having at least one high aspect ratio hole; directing an electron beam having a landing energy greater than 5000 eV into the high aspect ratio hole, the electron beam being directed in circular pattern within the hole, the radius of the circular pattern being less than ¼ the radius of the hole to deposit an elongate structure into the hole; directing an electron beam toward the work piece in a second pattern to fill the regions of the hole between the elongate structure and the hole side wall, to fill the hole without leaving voids in the fill material.

Some embodiments of the invention provide a charged particle beam system comprising a source of charged particles; a focusing column for directing a beam of charged particles toward a work piece, the work piece having at least one hole having an aspect ratio greater than 3:1; a gas delivery system for providing a precursor gas at the surface of the work piece; and a system controller programmed with instructions to control the charged particle microscope for directing the charged particle beam into the hole, the charged particle beam being directed to a region within the hole having an area less than the cross sectional area of the hole to decompose the precursor gas and deposit material in the hole, the charged particle beam being directed into the hole for a sufficient period of time to form an elongate structure that does not touch the side walls at the top of the hole.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of

We claim as follows:

1. A method of filling a hole using charged particle beam-induced deposition, comprising:
   providing a deposition precursor gas at the surface of the work piece;
   directing a charged particle beam into a hole having an aspect ratio greater than 3:1, the charged particle beam being directed to a region within the hole having an area less than the cross sectional area of the hole to decompose the precursor gas and deposit material in the hole, the charged particle beam being directed into the hole for a sufficient period of time to form an elongate structure that does not touch the side walls at the top of the hole.

2. The method of claim 1 in which further comprising directing the charged particle beam to cover an area extended beyond the edges of the hole to fill the region between the elongate structure and the hole side walls, thereby filling the hole without voids in the fill material.

3. The method of claim 1 in which directing the charge particle beam into the hole for a sufficient period of time to form an elongate structure comprises forming an elongate structure that does not contact the top walls of the hole, and further comprising directing the charged particle to an area that is a superset of the first area to finish filling the hole.

4. The method of claim 1 in which the hole comprises a cylindrical hole and in which directing the charged particle beam into the hole comprises directing an electron beam in a circular pattern, the diameter of the circular pattern being less than ½ the diameter of the hole.

5. The method of claim 1 in which the hole is a channel and in which directing the charged particle beam into the hole comprises directing an electron beam into the channel in a circular pattern having a diameter of less than ½ the channel width.

6. A method of filling a high aspect ratio hole, comprising:
   providing a deposition precursor gas at the surface of a work piece, the work piece having at least one high aspect ratio hole;
   directing an electron beam into the high aspect ratio hole, the electron beam being directed in first pattern to impact a region in the hole having a cross section area less than the entire cross sectional area of the hole to deposit an elongate structure into the hole;
   directing an electron beam toward the work piece in a second pattern to fill the regions of the hole between the elongate structure and the hole side wall, to fill the hole without leaving voids in the fill material.

7. The method of claim 6, in which directing an electron beam toward the work piece in a second pattern includes directing the electron beam in a second pattern covering an area that includes the entire hole.

8. The method of claim 6, in which:
   providing a deposition precursor gas at the surface of a substrate includes providing a precursor gas that decomposes in the presence of the electron beam to deposit a metal; and
   directing an electron beam in the first pattern includes directing an electron beam having a landing energy of greater than 5000 eV.

9. The method of claim 6, in which:
   providing a deposition precursor gas at the surface of a substrate includes providing a precursor gas that decomposes in the presence of the electron beam to deposit carbon; and
   directing an electron beam in the first pattern includes directing an electron beam having a landing energy of greater than 3000 eV.

10. The method of claim 6, in which directing an electron beam in the first pattern includes directing the electron beam in a circular pattern, the diameter of the circle pattern being less than ½ the diameter of the hole.

11. The method of claim 6, in which directing an electron beam in the first pattern includes directing the electron beam in a circular pattern, the diameter of the circle pattern being less than ¼ the diameter of the hole.

12. The method of claim 10 in which the hole is a channel and the diameter of the circle pattern is less than ½ the channel width.

13. The method of claim 11 in which the hole is a channel and the diameter of the circle pattern is less than ¼ the channel width.

14. A method of filling a high aspect ratio hole, comprising:
   providing a deposition precursor gas at the surface of a work piece, the work piece having at least one high aspect ratio hole;
   directing an electron beam having a landing energy greater than 5000 eV into the high aspect ratio hole, the electron beam being directed in circular pattern within the hole, the radius of the circular pattern being less than ¼ the radius of the hole to deposit an elongate structure into the hole;
   directing an electron beam toward the work piece in a second pattern to fill the regions of the hole between the elongate structure and the hole side wall, to fill the hole without leaving voids in the fill material.

15. A charged particle beam system comprising:
   a source of charged particles;
   a focusing column for directing a beam of charged particles toward a work piece, the work piece having at least one hole having an aspect ratio greater than 3:1;
   a gas delivery system for providing a precursor gas at the surface of the work piece; and
   a system controller programmed with instructions to control the charged particle microscope for:
      directing the charged particle beam into the hole, the charged particle beam being directed to a region within the hole having an area less than the cross sectional area of the hole to decompose the precursor gas and deposit material in the hole, the charged particle beam being directed into the hole for a sufficient period of time to form an elongate structure that does not touch the side walls at the top of the hole.

16. The charged particle beam system of claim 15 in which the instructions further comprise directing the charged particle beam to cover an area extended beyond the edges of the hole to fill the region between the elongate structure and the hole side walls, thereby filling the hole without voids in the fill material.

17. The charged particle beam system of claim 15 in which the instructions for directing the charged particle beam into the hole for a sufficient period of time to form an elongate structure comprises instructions for forming an elongate structure that does not contact the top walls of the hole, and further comprising directing the charged particle to an area that is a superset of the first area to finish filling the hole.

18. The charged particle beam system of claim 15 in which the hole comprises a cylindrical hole and in which directing the charged particle beam into the hole comprises directing an electron beam in a circular pattern, the diameter of the circular pattern being less than ½ the diameter of the hole.

19. The charged particle beam system of claim 15 in which the hole is a channel and in which directing the charged particle beam into the hole comprises directing an electron beam into the channel in a circular pattern having a diameter of less than ½ the channel width.

\* \* \* \* \*